US011486939B2

(12) United States Patent
Harris

(10) Patent No.: US 11,486,939 B2
(45) Date of Patent: Nov. 1, 2022

(54) SYSTEM AND METHOD OF DETERMINING AGE OF A TRANSFORMER

(71) Applicant: Aurtra Pty Ltd, Brisbane (AU)

(72) Inventor: Richard Harris, Brisbane (AU)

(73) Assignee: Aurtra Pty Ltd, Brisbane (AU)

( * ) Notice: Subject to any disclaimer, the term of this patent is extended or adjusted under 35 U.S.C. 154(b) by 477 days.

(21) Appl. No.: 16/629,482

(22) PCT Filed: Jul. 9, 2018

(86) PCT No.: PCT/AU2018/050707
§ 371 (c)(1),
(2) Date: Jan. 8, 2020

(87) PCT Pub. No.: WO2019/010523
PCT Pub. Date: Jan. 17, 2019

(65) Prior Publication Data
US 2021/0063496 A1 Mar. 4, 2021

(30) Foreign Application Priority Data
Jul. 9, 2017 (AU) ................................. 2017902684

(51) Int. Cl.
| | |
|---|---|
| *G01R 31/62* | (2020.01) |
| *G01N 33/28* | (2006.01) |
| *G01R 31/12* | (2020.01) |
| *H01F 27/12* | (2006.01) |
| *H01F 27/32* | (2006.01) |

(52) U.S. Cl.
CPC ......... *G01R 31/62* (2020.01); *G01N 33/2847* (2013.01); *G01R 31/1281* (2013.01); *H01F 27/12* (2013.01); *H01F 27/32* (2013.01)

(58) Field of Classification Search
CPC ............ G01N 33/2847; G01R 31/1227; G01R 31/1281; G01R 31/62; H01F 27/12; H01F 27/32; H01F 27/402
See application file for complete search history.

(56) References Cited

U.S. PATENT DOCUMENTS

2013/0243033 A1 9/2013 Asano, Jr.

FOREIGN PATENT DOCUMENTS

JP 2008066435 A * 3/2008 ............. G01N 33/28

OTHER PUBLICATIONS

International Search Report corresponding to International Patent Application No. PCT/AU2018/050707, dated Sep. 11, 2018 (4 pages).

(Continued)

*Primary Examiner* — Jermele M Hollington
*Assistant Examiner* — Courtney G McDonnough
(74) *Attorney, Agent, or Firm* — Nixon Peabody LLP

(57) ABSTRACT

A method of determining polymerisation of transformer insulation within a transformer. The method includes the steps of measuring a first and second moisture activity of oil in a transformer, and a first and second temperature of the transformer. The method further includes calculating the ratio of the gradients of the moisture equilibrium curves associated with the moisture activity and the temperature. The calculated ratio can then be used to characterise the polymerisation of the insulation and age of the transformer.

20 Claims, 8 Drawing Sheets

(56) References Cited

OTHER PUBLICATIONS

Written Opinion of International Searching Authority corresponding International Patent Application No. PCT/AU2018/050707, dated Sep. 11, 2018 (6 pages).
International Preliminary Report on Patentability corresponding to International Patent Application No. PCT/AU2018/050707, dated Oct. 11, 2019 (13 pages).
Lelekakis, N. et al.; "Aging Rate of Grade 3 Presspaper Insulation used in Power Transformers"; IEEE Transactions on Dielectrics and Electrical Insulation, vol. 2, No. 5, pp. 2355-2362; Oct. 1, 2014 (9 pages).
Martin, D. et al.; "Fundamental Concepts of Using Water Activity Probes to Assess Transformer Insulation Water Content"; IEEE Electrical Insulation Magazine, Bol. 32, Issue 3, pp. 9-15; Aug. 3, 2016 (8 pages).
Emsley, A.M. et al.; "Review: Kinetics and Mechanisms of the low-temperature degradation of cellulose"; CELLULOSE, vol. 1, Issue 1, pp. 26-56; Mar. 1, 1944 (31 pages).
Emsley, A.M. et al.; "Degradation of cellulosic insulation in power transformers; Part 3: Effects of oxygen and water on ageing in oil"; Proc. IEE Sci. Measur. Technol., vol. 147, pp. 115-119; 2000 (5 pages).

\* cited by examiner

SYSTEM AND METHOD OF DETERMINING AGE OF A TRANSFORMER

CROSS-REFERENCE TO RELATED APPLICATIONS

This application is a U.S. National Stage of International Application No. PCT/AU2018/050707, filed Jul. 9, 2018, which claims the benefit of Australian Patent Application No. 2017902684, filed Jul. 9, 2017, both of which are incorporated herein by reference in their entireties.

FIELD OF THE INVENTION

The present invention relates to a system and method of determining polymerisation of transformer insulation. In particular, the invention relates to determining the amount of polymerisation of transformer insulation without removing the transformer from service and visual inspections or insulation sampling.

BACKGROUND

Any references to methods, apparatus or documents of the prior art are not to be taken as constituting any evidence or admission that they formed, or form, part of the common general knowledge.

Considerable research has been conducted over the past 5 decades into the processes involved in the degradation of insulation within transmission and distribution transformers. This work is driven by the high cost of early replacement and unplanned failure of these assets which account for a significant percentage of a power transmission system's total cost. The target aim is to be able to accurately assess the state of a transformer while in-service so its life can be managed in the aim of total business cost efficiency.

An interesting aspect of modern transformer design is that best practice is still to use simple cellulose paper as the main winding insulation. Cellulose paper saturated with mineral oil remains the best, most affordable, winding insulation. However, as with all paper, the combination of heat, water and acids, causes damage to the polymer chains—breaking them down and destroying their mechanical and electrical properties. As the chains get shorter, the paper loses its mechanical strength and becomes brittle. Ultimately, fractures start to occur (as a result of mechanical vibrations) and within an operational transformer, these fractures concentrate electric fields and focus localised electric fields—ultimately causing insulation breakdowns. These breakdowns can ultimately avalanche to catastrophic transformer failure.

In the industry, it is well known that seeing inside a large transformer to assess its state is impossible without major engineering works.

Techniques such as off-line (taking the transformer temporarily out-of-service) oil and insulation sampling, off-line electrical measurement of the insulation status using high voltage and extremely sensitive test equipment, on-line (during service) measurement of micro-breakdowns, and online measurement of oil and paper insulation parameters are highly topical and the subject of considerable publication effort.

The most commonly used technique to assess the state of the transformer insulation is to measure the quantity of moisture in the oil, and use that to assess the level of moisture within the paper insulation. Knowing this over time can be used to assess the amount of damage that has been and is occurring to the insulation because of polymer chain breakdown (depolymerisation) or the chance of water bubbling and bubble precipitated breakdown. A typical method for assessing the moisture content of the oil is to sample the oil and send it for chemical analysis. Charts are available (developed over many decades) which relate the measured level to water in the oil to water content in paper and the need for maintenance. These charts are published by various organizations including the international standards bodies (IEEE and IEC).

The process of physical sampling and laboratory testing of oil is expensive and as-a-result can only be completed sporadically. Online techniques are considered much more commercially promising as they allow the continuous monitoring of status at much lower expense. Over the past 10 years relatively inexpensive probes have become available that can measure the temperature and water activity within the insulation oil with accuracy. These probes are inserted into the transformer oil flow. Once installed the approach is affordable and allows the continuous assessment of the water content in the paper. The most advanced technology that has been developed to date allows this data to be interpreted for life lost and depolarization since start of measurement. This technology uses a detailed understanding of the processes of decay in the transformer insulation, and using the state of the oil, estimates the damage that is occurring and how that will impact life and aging over time. This technology is seen as highly attractive to equipment owners.

However, many older transformers are of concern to asset owners. In Australia, for example, a very significant percentage of in-service transformers are over 50 years old and the record of their operation and general service history even a decade ago is often quite sketchy. As a result, applying a measurement system on the transformer during the last 20% of possible life, which can only assess the impacts since the measurement system was applied, is of limited use, unless an absolute measure of the insulation state using expensive off-line techniques is applied prior to installation. This adds significantly to the complexity and cost, and significantly reduces the utility, of applying on-line techniques widescale, and given the accuracy of single off-line assessments of insulation state is not high, provides an unsecure foundation for all later on-line measurement and status assessment.

OBJECT OF THE INVENTION

It is an aim of this invention to provide a system and method of determining polymerisation of transformer insulation which overcomes or ameliorates one or more of the disadvantages or problems described above, or which at least provides a useful commercial alternative.

Other preferred objects of the present invention will become apparent from the following description.

SUMMARY OF THE INVENTION

According to a first aspect of the present invention, there is provided a method of determining polymerisation of transformer insulation, the method comprising the steps of:
  measuring a first moisture activity of oil in a transformer;
  measuring a first temperature of the transformer;
  measuring a second moisture activity of oil in the transformer;
  measuring a second temperature of the transformer; and calculating a ratio of gradients of moisture equilibrium curves associated with the first moisture activity and the first temperature and the second moisture activity and the second temperature.

According to a second aspect of the present invention, there is provided a system adapted to determine polymerisation of transformer insulation, the system comprising:
  a transformer;
  at least one sensor adapted to measure moisture activity of oil and temperature of the transformer; and
  a processor configured to:
    receive a first moisture activity of oil in the transformer from the at least one sensor;
    receive a first temperature of the transformer from the at least one sensor;
    receive a second moisture activity of oil in the transformer from the at least one sensor;
    receive a second temperature of the transformer from the at least one sensor; and
    calculate a ratio of gradients of moisture equilibrium curves associated with the first moisture activity and the first temperature and the second moisture activity and the second temperature.

According to a third aspect of the present invention, there is provided a non-transitory computer readable medium with computer executable instructions stored thereon executed by a processor to perform a method of determining polymerisation of transformer insulation, the method comprising the steps of:
  accessing a database having a first moisture activity of oil and a first temperature associated with a transformer;
  accessing the database having a second moisture activity of oil and a second temperature associated with the transformer; and
  calculating a ratio of gradients of moisture equilibrium curves associated with the first moisture activity and the first temperature and the second moisture activity and the second temperature.

Preferably, the method further comprises the step of comparing the ratio of gradients with historical records or laboratory test data to estimate a level of polymerisation of insulation in the transformer.

Preferably, the method further comprises the step of calculating a first water content of oil based on the first moisture activity and the first temperature. Preferably, the method further comprises the step of calculating a second water content of oil based on the second moisture activity and the second temperature.

Preferably, the ratio of gradients is calculated using $$R = \frac{MCO_{T2} - MCO_{T1}}{MCO_{T1}},$$

where $MCO_{T1}$ is the first Water Content of the Oil at the first temperature T1 and $MCO_{T2}$ is the second Water Content of the Oil at the second temperature T2.

Preferably, the processor is configured to determine whether the ratio or level indicates a transformer near the end of its life. More preferably, the ratio or level is below a threshold value. Even more preferably, determining if the ratio or level is approaching 1.

Preferably, the processor is configured to at least one of communicate and notify when the ratio or level indicates a transformer near the end of its life. More preferably, the processor is configured to at least one of communicate and notify when the ratio or level indicates a transformer requiring maintenance.

Preferably, determining whether the ratio or level indicates a transformer near the end of its life comprises comparing the level or ratio of gradients of moisture equilibrium curves to a historical level or ratio of gradients of moisture equilibrium curves.

Preferably, notifying when the ratio or level indicates a transformer near the end of its life or requiring maintenance comprises presenting an alert or notification to a user.

Preferably, the first and second water content of oil are calculated using $$WCO = a_w \times 10^{A - \frac{B}{T}},$$

wnere $a_w$ is water activity, WCO is the water content of the oil (equal to MCO), A and B are constants for the type of oil used, and T is temperature of the oil in Kelvin.

Preferably, the method further comprises the step of calculating a first moisture equilibrium curve associated with the first water content of oil.

Preferably, the method further comprises the step of calculating a second moisture equilibrium curve associated with the second water content of oil.

Preferably, the method further comprises the step of plotting the first and second moisture equilibrium curves.

Preferably, the method further comprises the step of graphically displaying the plots of the first and second moisture equilibrium curves.

In a fourth aspect, the present invention provides a method for determining polymerisation of insulation of a transformer, the method comprising the steps of:
  measuring temperature data of a transformer at predefined intervals and simultaneously measuring water activity of oil data of the transformer;
  storing the water activity data and the temperature data in a database;
  accessing the water activity data and the temperature data from the database
  calculating a difference between the temperature data at a first of the predefined intervals and the temperature data at a second of the predefined intervals;
  whereby:
    if the difference is not equal to 0,
    calculating a ratio of gradients of moisture equilibrium curves associated with the water activity data and the temperature data at the first of the predefined intervals and the water activity data and the temperature data at the second of the predefined intervals; and
    if the difference is equal to 0, calculating a difference between the temperature data at the first of the predefined intervals and the temperature data at a third of the predefined intervals.

Preferably, the method further comprises the steps of calculating a first water content of oil based on the temperature data and the water activity of oil data measured at the first of the predefined intervals; and
calculating a second water content of oil based on the temperature data and the water activity of oil data measured at the second of the predefined intervals.

BRIEF DESCRIPTION OF THE DRAWINGS

By way of example only, preferred embodiments of the invention will be described more fully hereinafter with reference to the accompanying figures, wherein.

Preferred features, embodiments and variations of the invention can be discerned from the following Detailed Description which provides sufficient information for those skilled in the art to perform the invention. The Detailed Description and associated figures are not to be regarded as limiting the scope of the preceding Summary of the Invention in any way.

DETAILED DESCRIPTION OF THE PREFERRED EMBODIMENTS

The present invention relates to a system and method of determining the degree of polymerisation of transformer insulation.

More particularly, the invention relates to determining polymerisation of transformer insulation without removing the transformer from service and without internal visual inspections or insulation sampling.

Figure 1:
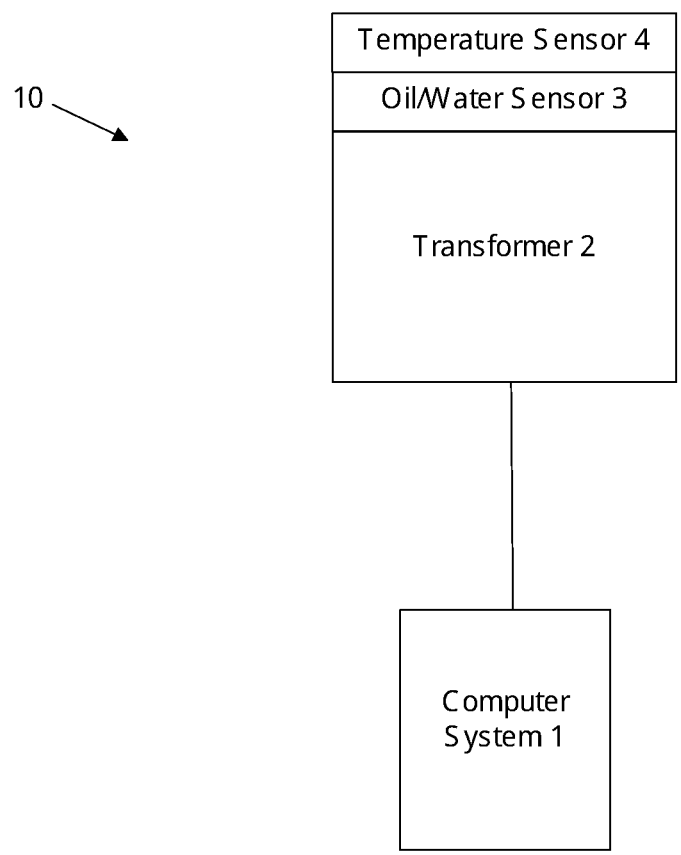
FIG. 1 illustrates a block diagram of a system in accordance with an embodiment of the present invention.

FIG. 1 shows a block diagram of a system 10 in which measurement of transformer data and analysis of said data takes places in accordance with an embodiment of the present invention. The system 10 includes a transformer 2 (or series of transformers) having a first oil sensor in the form of a capacitive sensor 3 and a second sensor in the form of a temperature sensor 4, and a computer system 1. The temperature sensor can be any sensor suitable for measuring the temperature of an oil-filled transformer, such as a fibre-optic temperature sensor, for example.

The capacitive oil sensor 3 directly measures and collects water activity data (also known as moisture activity) of the oil and the temperature sensor 4 measures and collects the temperature data of the transformer. This water activity data and temperature data are then communicated to the computer system 1 by any suitable means for storage and analysis by the computer system 1.

Figure 2:
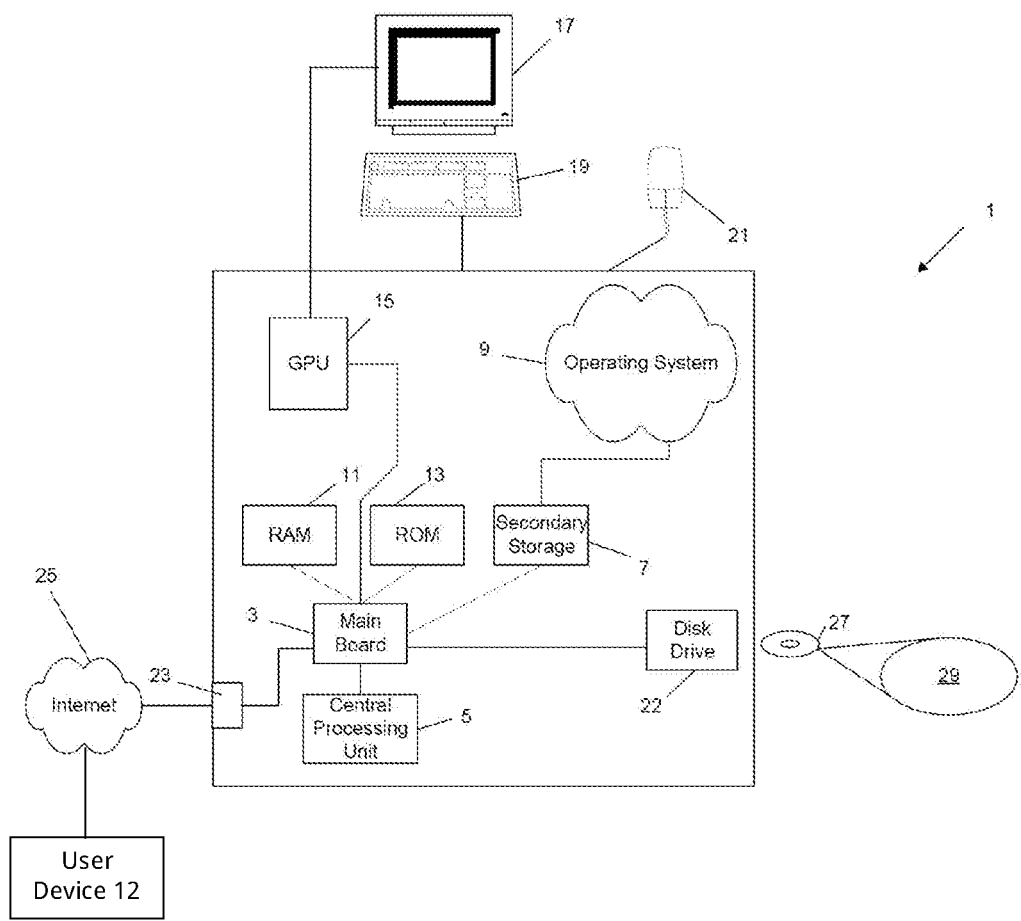
FIG. 2 illustrates an exemplary computer system for implementing a method according to an embodiment of the present invention.

Referring now to FIG. 2, there is shown a block diagram of an exemplary computer system 1 for carrying out a method according to an embodiment of the invention that will be described.

It will be understood that the computer system 1 comprises an exemplary electronic processor-based system for carrying out the method. However, the method may also be readily performed with other electronic processor-based systems. Such systems may include, without limitation, mainframe computer, supercomputer, cloud-server, desktop, tablet, laptop and netbook computational devices and cellular smart phones.

The computer system 1 includes a main board 3 which includes circuitry for powering and interfacing to at least one onboard processor 5. The at least one onboard processor may comprise two or more discrete processors or processors with multiple processing cores.

The main board 3 acts as an interface between microprocessor 5 and secondary memory 7. The secondary memory 7 may comprise one or more optical or magnetic, or solid state, drives. The secondary memory 7 stores instructions for an operating system 9. The main board 3 also communicates with random access memory 11 and Read Only Memory 13. The ROM 13 typically stores instructions for a Basic Input Output System (BIOS) which the microprocessor 5 accesses upon start up and which preps the microprocessor 5 for loading of the operating system 9.

The main board 3 also interfaces with a graphics processor unit 15. It will be understood that in some systems the graphics processor unit 15 is integrated into the main board 3.

The main board 3 will typically include a communications adapter, for example a LAN adaptor or a modem, that places the computer system 1 in data communication with a computer network such as the internet 25.

In embodiments hosted in a cloud server or server, any or all of the above parts or functions may be generated virtually or not at all as needed to ensure computational functionality and database integrity.

A user of the computer system 1 interfaces with it by means of keyboard 19, mouse 21 and display 17.

A user may also receive information delivered via the internet 25 to a user device 12 (such as a smartphone, PC or tablet).

The user of system 1 may operate the operating system 9 to load a processor executable set of instructions 29. The instructions 29 are provided as tangible instructions borne upon a computer readable media such as optical disk 27. Alternatively it might also be downloaded via port 23 or internet 25.

The instructions 29 include instructions for the microprocessor 5 and possibly for the GPU 15 to analyse and manipulate data collected from the sensors 3 and 4.

Figure 3:
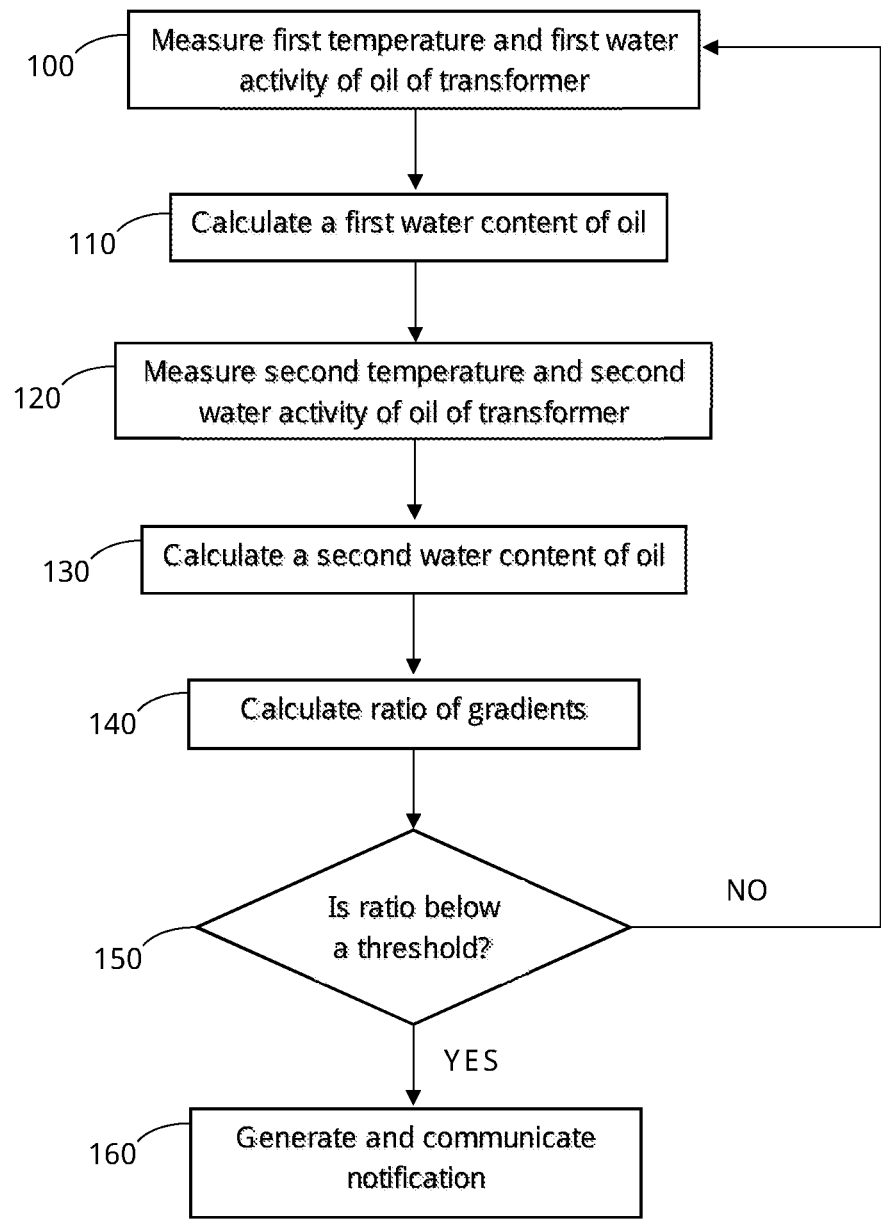
FIG. 3 illustrates a flowchart of a method according to an embodiment of the present invention.

Turning to FIG. 3, there is shown a flow chart illustrating an embodiment of the present invention for the system described in FIG. 1. In the illustrated embodiment, upon program initiation, in function step 100, the sensors in the transformer (such as oil sensor 3 and temperature sensor 4, for example) measure a first temperature and a first water activity of oil of the transformer at the first temperature. These measurements are stored in a database for analysis at a later time.

Next, at function step 110, the system calculates a first water content of oil based on the measurements of the first temperature and first water activity.

In subsequent function step 120, the sensors in the transformer measure a second temperature and a second water activity of oil of the transformer at the second temperature. Again, these measurements are stored in a database for analysis.

Additionally, the processing system calculates a second water content of oil based on the measurements of the second temperature and second water activity at function step 130.

At step 140, using the calculated first and second water content of oil data, the system calculates a ratio of the gradients of moisture equilibrium curves. An explanation of these calculations is given below.

At step 150, the processor then determines whether or not the ratio has fallen below a predetermined threshold value (e.g. 1.1). The threshold value indicates when the transformer insulation is approaching the end of its life and should be replaced. If the ratio has not fallen below the threshold value, the program returns to step 100. However, if the ratio has fallen below the threshold value, at step 160, the processor generates and communicates a notification to a user to alert them that the transformer insulation state may be approaching the end of its usable life and need to be replaced, for example.

Figure 4:
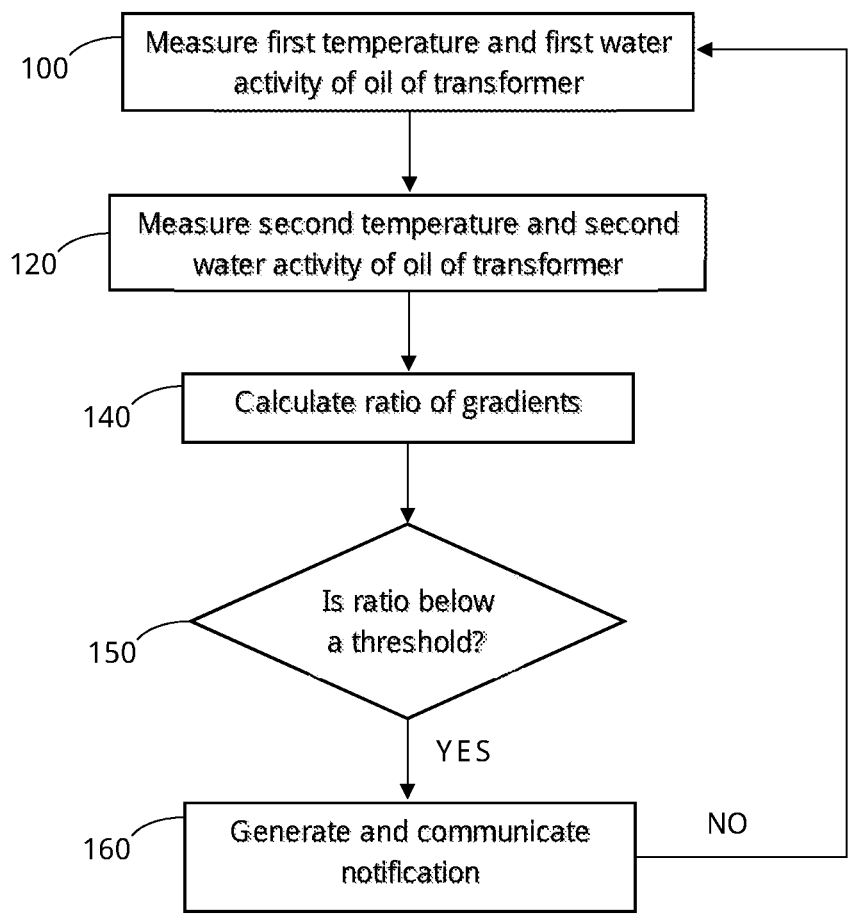
FIG. 4 illustrates a flowchart of another method according to an embodiment of the present invention.

Turning to FIG. 4, there is shown a flow chart illustrating a method which is an embodiment of the present invention for the system described in FIG. 1. This method is substantially similar to the method of FIG. 3 but omits steps 110 and 130.

As a result, at step 140, the ratio of gradients is calculated directly from the first and second moisture activity and first and second temperature without calculating the water content of oil associated with these data points.

Figure 5:
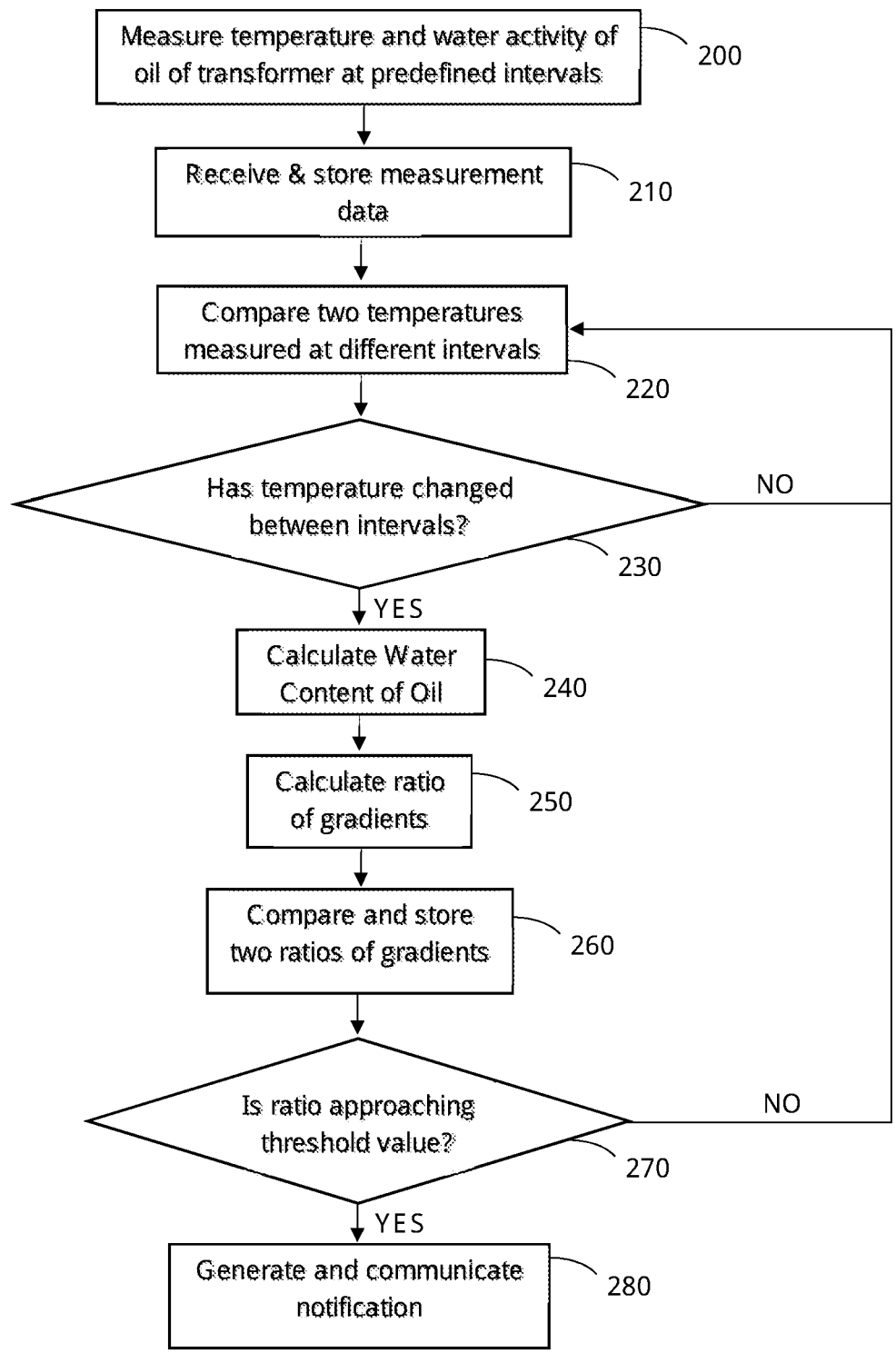
FIG. 5 illustrates a flowchart of a third method according to an embodiment of the present invention.

Turning to FIG. 5, there is shown another flow chart illustrating a further embodiment of the present invention for the system described in FIG. 1.

In the illustrated embodiment, upon program initiation, in function step 200, the sensors in the transformer repeatedly measure the temperature and water activity of the oil of the transformer at predefined intervals. Each of these measurements are stored in a database of a computer system (such as computer system 1, for example) for analysis at a later time at step 210.

Next, at function step 220, the system compares two temperature measurements taken at distinct time intervals. At step 230, the system determines whether the temperature has changed between the two intervals. If the temperature has remained the same, the program repeats step 220 and compares another two temperatures. However, if the temperature has changed in specific ways (e.g. substantially between one time interval and the next), the program moves onto step 240 and calculates the water content of oil for each temperature using the associated water activity data collected earlier.

Subsequently, the system uses the calculated water content of oil to calculate a ratio of the gradients of moisture equilibrium curves associated with the two sets of temperatures and water activity data.

Next, at step 260, the system compares the recently generated ratio with a historical ratio stored in the database of the computer system.

Using the comparison of the two ratios, at step 270, the computer system determines whether the ratio is approaching or has reached a threshold value indicating that the insulation of the transformer is nearing or has reached the end of its usable life. If the ratio does not indicate that the insulation is nearing the end of its life, the computer system returns to step 220. However, if the ratio has fallen below the threshold value, at step 280, the processor generates and communicates a notification to a user to alert of the state of the transformer as it approaches the end of its usable life.

Figure 6:
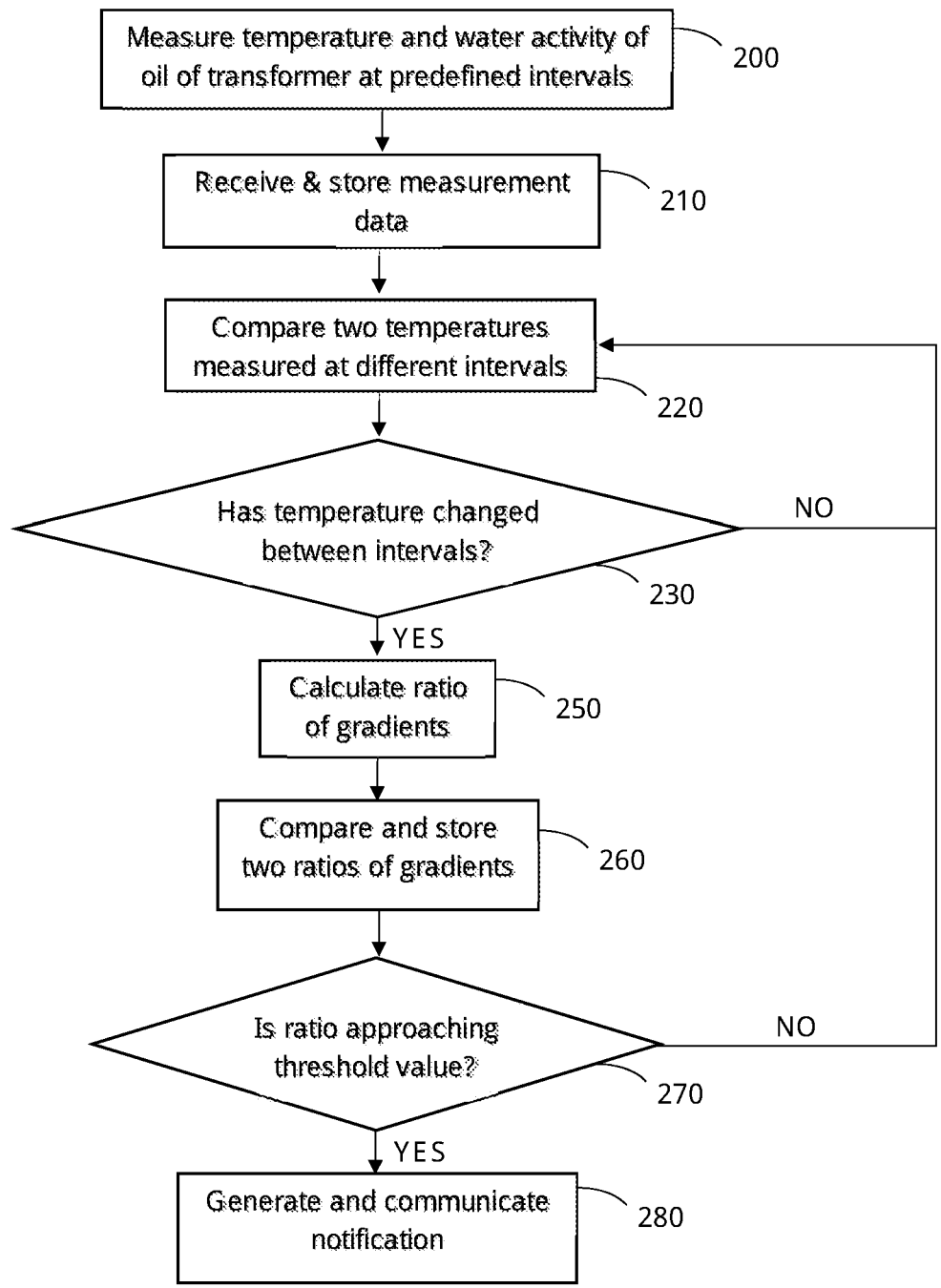
FIG. 6 illustrates a flowchart of a fourth method according to an embodiment of the present invention.

Referring now to FIG. 6, there is shown a flow chart illustrating a method which is substantially similar to the method in the flowchart of FIG. 4 but omits step 240.

As a result, at step 250, the ratio of gradients is calculated directly from the first and second moisture activity and first and second temperature without calculating the water content of oil associated with these data points.

The methods and systems described above use the reaction of the insulation to changes of temperature to decode the insulation age. This reaction can be pattern mapped to the absolute state of the paper insulation and the actual life left given normal operating conditions. This process can be repeated continuously as the asset operates over time, allowing measurement noise and non-linearity's to be filtered, and when linked with best-practice life lost and rate of depolymerisation calculations, to provide an accurate, multi-dimensional picture of the transformers state.

One historical inaccuracy with the existing process of converting the water content of the oil to the water content of the paper is that the relationship with the age of the paper was not well understood. Most testing was completed with new or lightly aged paper on the assumption that age was not a major contributor to errors.

Figure 7:
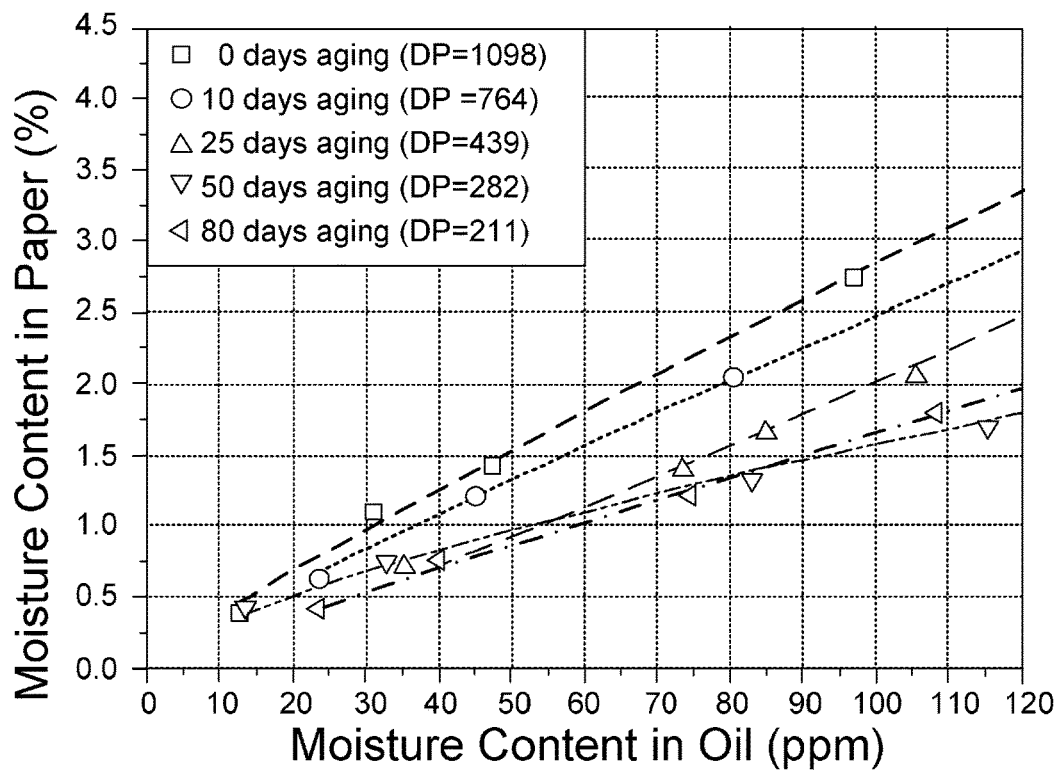
FIG. 7 illustrates moisture equilibrium curves of mineral oil-paper insulation at 55 degrees Celsius.

Turning briefly to FIG. 7, the Moisture Equilibrium Curves of Mineral oil-paper at a specific temperature for insulation of different age (polymerization levels) are shown. New paper has an average polymerization figure of near 1000. Paper is considered at the end of its life when the polymerization figure reduces to less than 300. This data is used in a very conventional way to allow the moisture content of the paper to be calculated more accurately from a measurement of the moisture in the oil, when the system is at steady state (that is after a period of time to allow the moisture in the paper and the oil to come to equilibrium).

Curves of a similar type can be produced for different temperatures. A series of curves is needed to provide the calculation given the steady state temperature is highly variable and dependent on transformer load and on ambient (environment) temperature.

The methods described herein use the basic (roughly) linear shape of the relationship between Water Content in Oil (WCO) and Water content in Paper (WCP) (although it is not required as an absolute mathematical necessity as the technique could also be made to work for other mathematical model of the relationship such as the polynomial). See FIG. 7 for the relationship at 55 degrees C. which is very close to the first approximation, linear.

These curves show that the relationship between Moisture Content of the Oil (MCO) and the Moisture Content of the Paper (MCP) is roughly or substantially linear and in-effect (in this case, as a first order approximation) simply proportional (as the y intercept is at the origin that is at zero MCO it is axiomatically correct that there will also be zero MCP).

Figure 8:
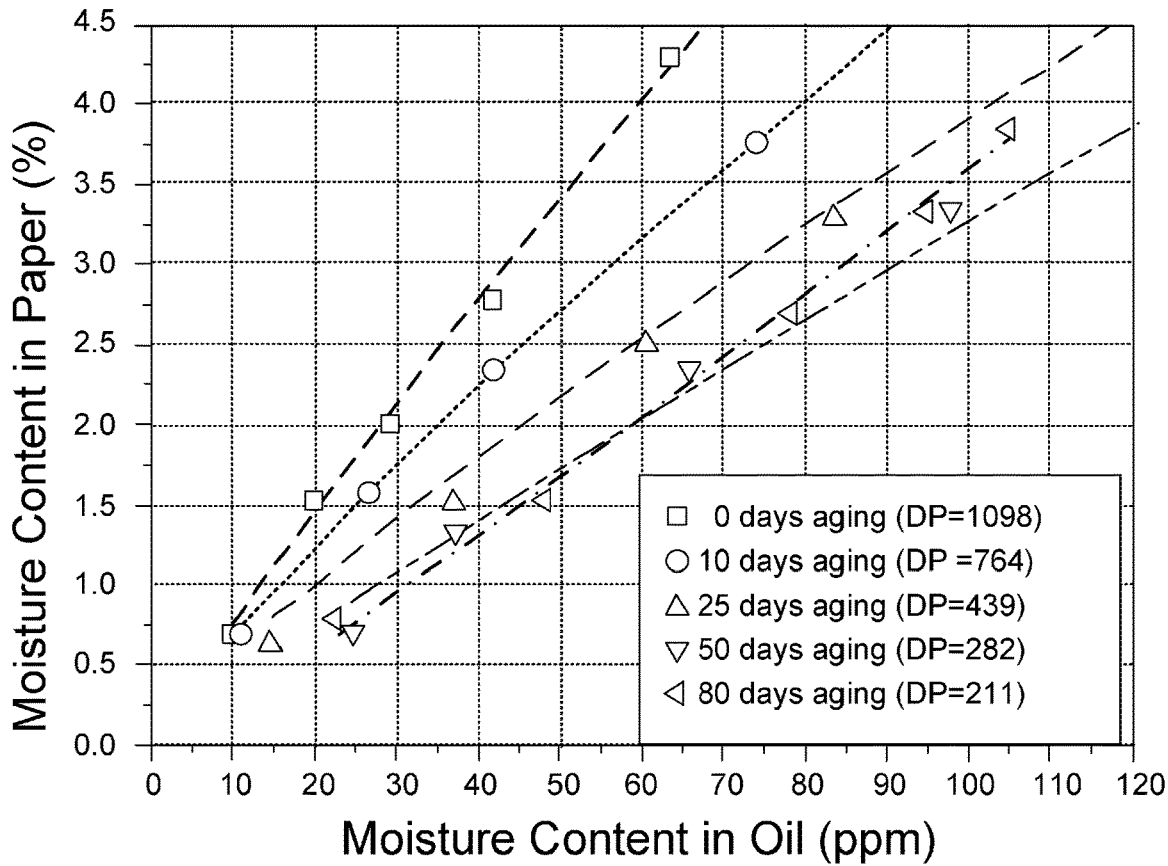
FIG. 8 illustrates moisture equilibrium curves of mineral oil-paper insulation at 85 degrees Celsius.
Figure 9:
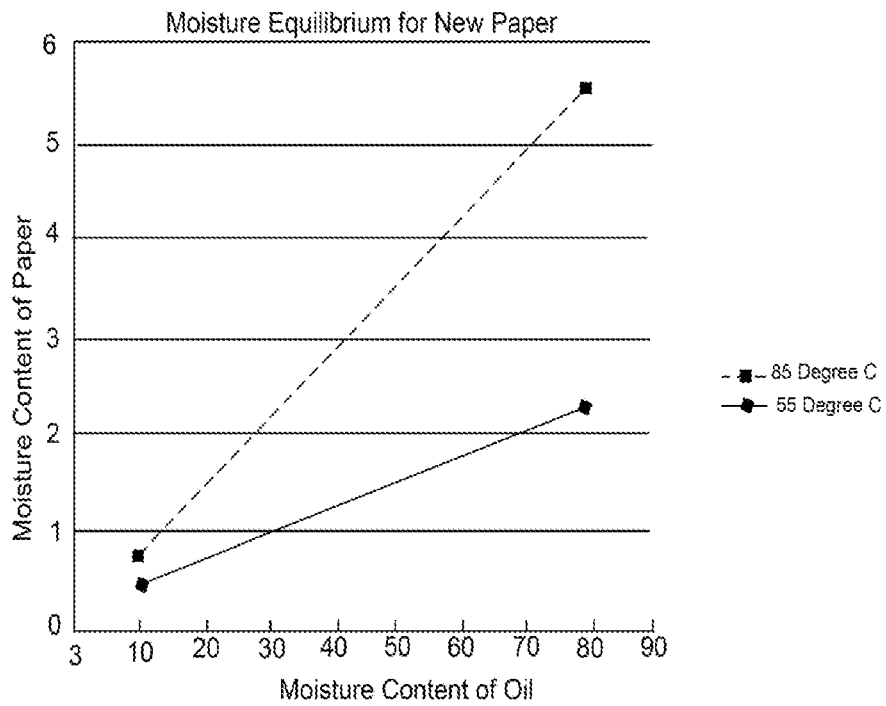
FIG. 9 illustrates moisture equilibrium curves of new paper insulation in mineral oil-paper insulation at 55 and 85 degrees Celsius.
Figure 10:
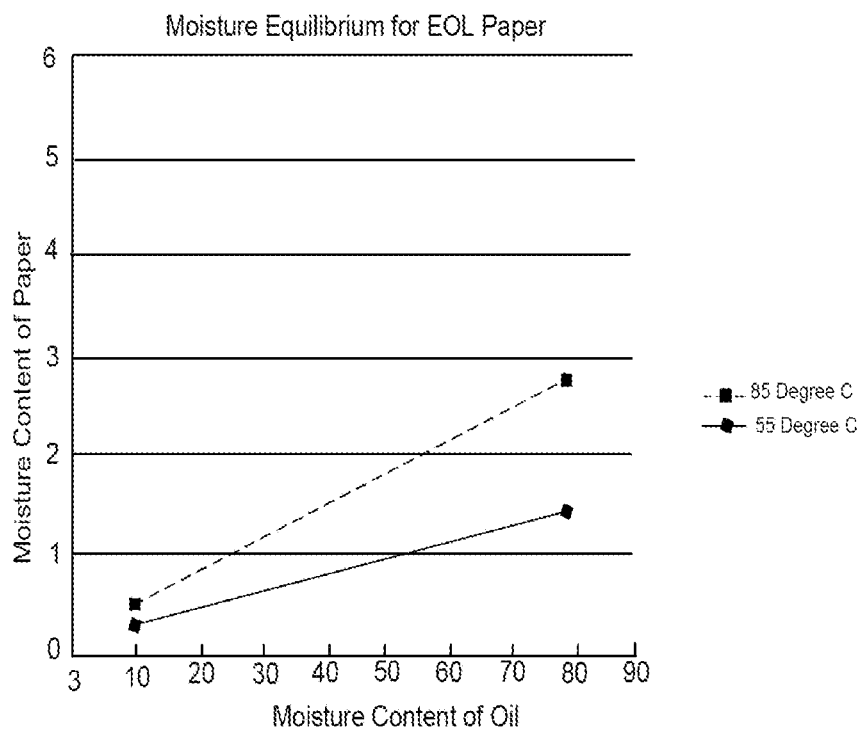
FIG. 10 illustrates moisture equilibrium curves of end-life paper insulation in mineral oil-paper insulation at 55 and 85 degrees Celsius.

Conventional transformer status assessment uses these relationships to assess the amount of water in the insulation from the water content of the oil, using an assumption of insulation age. The moisture content in the oil is measured along with temperature, then using figures such as FIGS. 7 and 8, the moisture content of the transformer insulation can be calculated. This can then be used to estimate (1) the need for maintenance (specifically off-line active drying of the transformer and fixing of seals etc.), (2) the amount of damage further use will cause over time if maintenance is not completed and (3) the chance of catastrophic failure under transient overload due to bubbling. Historically this is done sporadically as needed to drive maintenance planning. However, the methods described allow these curves to be re-plotted as shown in FIGS. 9 and 10. These plots show the curves of new paper at two temperatures 55 and 85 degrees C., and end of life paper (DP=300) at the same temperature pairs. Plots can be generated for any temperature pairs and for different levels of polymerization of the paper using further experimentation or estimated with reasonable accuracy using extrapolation between stepped measurements.

The relationships between the gradient of the lines in FIGS. 9 and 10 are critical to the methods described herein. For example, the relative difference (R) in the gradients (i.e. the ratio of the gradients) between the 55 and 85 degrees Celsius lines in FIG. 9, using the formula shown in Eq. 1 (effectively relative difference) is 1.638, but the same calculation using the data of FIG. 10 at the paper's end-of-life is 1.05. In effect, as the paper gets older, the amount of moisture the paper can absorb as a function of temperature changes. This is an empirically sensible relationship as aging causes the paper to mechanically breakdown and this causes a change in the way water molecules can bond to its surface.

The methods described herein used to calculate the age of the paper relies on the fact that this proportional relationship of the gradients between the moisture content in paper to the moisture content in the oil is independent of the Moisture Content of the paper because the functions are both straight lines. The ratio is only dependent on the two temperature end points (which are known or can be measured during any practical temperature change event accurately) and on paper insulation polymerization level (which is unknown).

It has been found that that during a temperature change, the actual water content of the paper insulation does not change significantly. The basis for this counter-intuitive assumption is discussed later. Accepting this assumption to be true allows the relationship of the gradients of the curves to be uncovered through the simple measurement of the water content of the oil before and after the temperature change over the transition.

$$R = \frac{G_{T1} - G_{T2}}{G_{T2}} \qquad \text{Eq. 1}$$

where $G_{T1}$=Gradient at Temperature 1, $G_{T2}$=Gradient at Temperature T2.

If a measurement of the water content of the oil before or after the temperature change is measured after sufficient time has passed for equalization between the paper and oil moisture vapor pressure to occur), then the gradient of the moisture equilibrium relationship at that temperature can be calculated using Eq. 2 from this single data point (using the other know data point at the origin).

$$G_{Tx} = \frac{MCP_{Tx} - 0}{MCO_{Tx} - 0} \qquad \text{Eq. 2}$$

$$G_{Tx} = \frac{MCP_{Tx}}{MCO_{Tx}}$$

where $G_{Tx}$ is gradient at temp x, $MCP_{Tx}$ is the Moisture content of the Paper at Temperature x, $MCO_{Tx}$ is the Moisture Content of the Oil at temperature x, and 0,0 being a known point on all curves being zero water content in oil showing zero water content in the paper.

Substituting Eq. 2 into Eq. 1 at the before and after temperatures, and assuming that the Water Content of the Paper (WCP) stays constant during the temperature, provides Eq. 3. Therefore if the Moisture Content of the Oil (MCO) measurements before and after the change in temperature from 55 to 85 degrees are taken after sufficient time to ensure that the system is in equilibrium at the time of measurement, then the ratio calculated by Equation 3 will provide a direct indication of the ratio of the gradients of the Moisture Equilibrium Curves and therefore a direct indication of level of polymerization within the insulation.

$$R = \frac{G_{T1} - G_{T2}}{G_{T2}} \qquad \text{Eq. 3}$$

$$R = \frac{(MCP_{T1}/MCO_{T1}) - (MCP_{T2}/MCO_{T2})}{MCP_{T2}/MCO_{T2}}$$

Assuming $MCP_{T1} = MCP_{T2}$ $$R = \frac{((1/MCO_{T1}) - (1/MCO_{T2}))}{1/MCO_{T2}}$$

$$R = \frac{(MCO_{T2} - MCO_{T1})}{MCO_{T1}}$$

For example, if a transformer experiences a temperature step change from 55 to 85 degrees Celsius which results in moisture on oil changes from 30 ppm to 70 ppm, Eq. 1 can be used to calculate a moisture change ratio of 1.5 {(70-30)/30=1.5}. This size change indicates that the paper insulation is near new. However, if under the same test the moisture in the oil changes from 27 to 55, the moisture in oil ratio associated with the change as per Eq. 2 will be (55–27)/27=1.04 indicating the paper insulation is near end of life. Therefore, using the methods described herein allows the age of the insulation to be estimated by two simple measurements of water content in the oil, before and after a step change.

The techniques described herein could also be applied after any temperature change where before and after water vapor equilibrium has been achieved within the transformer and accurate measurements can be taken. It may also be applied before equilibrium is achieved before or after a temperature change as long as a reasonable estimate of the final WCO can be made once equilibrium would have been achieved (from extrapolation of final WCO from WCO measurement during the equalisation period, for example).

As stated above, the technique described is based on the observed approximately linear nature of the water equilibrium curves in combination with the observation that the water content of the paper does not change significantly during short time periods over which the technique is applied. However, the technique could be applied in a similar way using other mathematical models of the water equilibrium curves on the same basis. For example, the water equilibrium curves could be modelled conceivably with high order polynomial (rather than the first order polynomial (a straight line) as described) or logarithmic equations. In such cases the higher order components of the polynomials or the exponent of the logarithmic function will be used to create a ratio of the gradients (or conceivably a ratio of higher order derivatives) between the moisture content at the two temperatures.

Using the above technique, the ratio could similarly be compared against historical (laboratory test) data to provide an estimate of the polymerisation or state of the transformers insulation. The term ratio of gradients therefore is considered (within the context of the present specification) to describe the technique irrespective of the mathematical model used for the moisture equilibrium curves for comparing the propensity of the insulation to absorb water at different temperatures, and to use the ratio of this propensity over temperature change, to ascertain insulation state and polymerisation.

Within the description the term ratio of gradients is specifically apt however as it reads directly to the ratio of the first derivative of the moisture equilibrium curves which, for the preferred embodiment, are approximated as straight lines.

To apply the methods practically, a system (such as system 10, for example) is needed which continuously records Moisture Content in Oil and temperature. As described, post processing can then be used to look day to day for step changes in the transformer temperature and provide continuous re-estimates of the insulation age.

Over any moderate period of time (<3 months), excluding serious aging events that may materially change the age of the paper, estimates can be averaged to provide an accurate assessment of insulation age. Historically the moisture content of the Oil is measured directly (typically using sampling and chemical analysis), and then with an estimate of age, the moisture content of the paper is calculated. However, this method of collecting measurements is typically done at one temperature (on or off line) and is too sporadic and time consuming to be useful for the new approach.

As an alternative, the relationship between MCO and the moisture activity of the oil (humidity of the oil in layman terms) has also been carefully studied and is well documented. The basic relationship between these parameters is providing in Eq. 4, where aw is water activity, WCO is the water content of the oil (equal to MCO), A and B are constants for the type of oil used, and T is temperature of the oil in Kelvin.

$$WCO = a_w \times 10^{A-\frac{B}{T}} \qquad \text{Eq. 4}$$

Moisture activity ($a_w$) is a parameter that can be measured using moisture activity in oil probes developed for the petro-chemical industry. These probes use a capacitive sensor to directly measure the water activity through a relationship that sees the permittivity of the dielectric in a sensor capacitor change in response to the water dissolved in a surrounded medium.

These probes and the relationship of Eq. 4 allow the moisture/water content of the oil to be continuously monitored over time.

Alternatively, it is possible through substitution of Eq.4 into Eq.3 to calculate R directly from water/moisture activity as provided in Eq.5.

$$R = \frac{(MCO_{T2} - MCO_{T1})}{MCO_{T1}} \qquad \text{Eq. 5}$$

$$R = \frac{\left(a_{wT2} \times 10^{A-\frac{B}{T2}} - a_{wT1} \times 10^{A-\frac{B}{T1}}\right)}{a_{wT1} \times 10^{A-\frac{B}{T1}}}$$

$$R = \frac{\left(a_{wT2} \times 0^{\left(\frac{B}{T1}-\frac{B}{T2}\right)} - a_{wT1}\right)}{a_{wT1}}$$

A further benefit of methods described herein, that is not immediately evident, is that they can be used to improve historical techniques such as for estimating life-lost and total depolymerisation of insulation over a period of time. When combined with these calculations from the same water activity measurements, improved additional accuracy of all predictions can be generated.

As an example, certain techniques may be used to indicate over a period of time the amount of depolymerisation of the paper which has occurred, this can be compared to the difference in the absolute depolymerisation estimates calculated using the newly developed technique to improve the accuracy of both or improve input assumptions to both techniques to generate improved correlation (such as oil state, oil type, oil impurity estimations etc).

As mentioned previously the technique assumes that during the temperature change, the water content of the paper does not change. This is an important counterintuitive assumption fundamental to the invention as without it the ratio of the gradient of the moisture equilibrium curves in FIGS. 9 and 10 can't be uncovered from simple "before and after temperature change" water activity or water content in oil measurements.

This assumption is valid because within a transformer, the vast majority of the moisture is held in the paper due to the paper's propensity to absorb water in comparison with oil which is hydrophobic. As an example, it has been found that a transformer with several tons of paper insulation may hold as much as 250 kg of water absorbed in the paper (up to 10% WCP by weight), but at the same time only 2 kg of water absorbed in the oil. Water in a transformer comes from either degradation of the paper or from exposure of the oil to humid atmosphere. But as it is generated or enters, the paper insulation in effect keeps the oil relatively free of water (much like how paper towel dries a dish). So even if the oil is completely saturated with oil (e.g. just before water starts to form (precipitate out) as bubbles of water within the oil), there may be only at most a few kilograms of water in the oil, more than 100 less than is in the paper.

As a result, no matter what occurs during the period of the sample WCO or Aw pair at two temperatures, very little water relatively can move out of the paper into the oil without the oil becoming saturated during any reasonable amount of time (e.g. hours or days). Indeed, the amount of water movement required to drive the oil from completely dry to completely saturated is a very small fraction of the total oil held in the insulation of a wet transformer, <1% of water available). This level of change is inconsequential to the accuracy of the methods described herein. As a result, the water content of the paper will remain fairly constant over the short term (irrespective of temperature) until either water is added to the system (cellulose breakdown or seal leak over time), or water is removed by active drying of the oil during maintenance. These processes can be discounted during a short-term temperature change of a maximum of a few days in duration.

A final important assumption underpinning the invention is that defined temperate steps occur from time to time in the operational life of the transformer to provide a clear polymerization signal. Fortunately, such steps in temperatures are quite common in practice including for example when the transformer is activated from a backup or off-line state, after works at the site which required electrical shutdown, during daily operational cycles (between the cool low load periods to high load during the latter part of a hot day), during step changes in load due to other equipment failure, during the passage of weather fronts in the area the transformer is located, where the ambient temperature and the consumer load change quickly, or during the application of a new or intermittent loads.

Using the methods and systems described herein, it is envisioned that transformer life can be extended nearly indefinitely.

In this specification, any reference to "historical data", "historical levels" or "historical ratios" is intended to refer to historical data relevant to the performance of the specific transformer under test, and historical data collected through laboratory testing and other experimentation data completed and documented in the world's engineering and science publications, and test data and analysis results developed and collected and stored by Aurtra, etc.

In this specification, adjectives such as first and second, left and right, top and bottom, and the like may be used solely to distinguish one element or action from another element or action without necessarily requiring or implying any actual such relationship or order. Where the context permits, reference to an integer or a component or step (or the like) is not to be interpreted as being limited to only one of that integer, component, or step, but rather could be one or more of that integer, component, or step, etc.

The above detailed description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention.

In this specification, the terms 'comprises', 'comprising', 'includes', 'including', or similar terms are intended to mean a non-exclusive inclusion, such that a method, system or apparatus that comprises a list of elements does not include those elements solely, but may well include other elements not listed.

Throughout the specification and claims (if present), unless the context requires otherwise, the term "substantially" or "about" will be understood to not be limited to the specific value or range qualified by the terms.

The invention claimed is:

1. A method of determining polymerisation of transformer insulation, the method comprising the steps of:
    measuring a first temperature of a transformer;
    measuring a first moisture activity of oil in the transformer at the first temperature;
    measuring a second temperature of the transformer;
    measuring a second moisture activity of oil in the transformer at the second temperature,
    wherein a moisture content of paper of the transformer is not measured or calculated; and
    calculating a ratio of gradients of moisture equilibrium curves associated with the first moisture activity and the first temperature, and the second moisture activity and the second temperature,
    wherein the moisture content of paper of the transformer is assumed to be substantially constant between the first temperature and the second temperature, and
    wherein the ratio indicates the degree of polymerisation of transformer insulation.

2. The method of claim 1, wherein the ratio of gradients is the ratio of the moisture equilibrium curves modelled using a linear relationship between a water content of oil and a water content of paper.

3. The method of claim 1 further comprising the step of comparing the ratio of gradients with historical records or laboratory test data to estimate a level of polymerisation of insulation in the transformer.

4. The method of claim 1 further comprising the step of determining if the ratio indicates the insulation of the transformer requires maintenance.

5. The method of claim 4, wherein determining if the ratio indicates the insulation of the transformer requires maintenance comprises determining if the ratio has fallen below a threshold value.

6. The method of claim 5, wherein determining if the ratio indicates the insulation of the transformer requires maintenance comprises comparing the ratio of gradients to a historical ratio of gradients and determining if the ratio of gradients is approaching a threshold value.

7. The method of claim 4, further comprising the step of communicating and notifying when the ratio indicates the insulation of the transformer requires maintenance.

8. The method of claim 7, wherein the step of communicating and notifying comprises presenting an alert or notification to a user device.

9. The method of claim 1, further comprising the steps of:
    calculating a first water content of oil based on the first moisture activity and the first temperature; and
    calculating a second water content of oil based on the second moisture activity and the second temperature.

10. The method of claim 9, further comprising the steps of:
    calculating a first moisture equilibrium curve associated with the first water content of oil calculated from the first moisture activity measurement; and
    calculating a second moisture equilibrium curve associated with the second water content of oil calculated from the second moisture activity measurement.

11. The method of claim 9, wherein the first and second water content of oil are calculated using $$WCO = \alpha_w \times 10^{A-\frac{B}{T}}$$

where $\alpha_w$ is moisture activity, WCO is the water content of the oil, A and B are constants for the type of oil used, and T is temperature of the oil in Kelvin.

12. The method of claim 1, wherein the ratio of gradients is calculated using $$R = \frac{MCO_{T2} - MCO_{T1}}{MCO_{T1}},$$

where $MCO_{T1}$ is the first Water Content of the Oil at the first temperature T1 and $MCO_{T2}$ is the second Water Content of the Oil at the second temperature T2.

13. The method of claim 1, wherein the ratio of gradients is calculated using $$R = \frac{\left(a_{wT2} \times 10^{\left(\frac{B}{T1} - \frac{B}{T2}\right)} - a_{wT1}\right)}{a_{wT1}}$$

where $a_{wT1}$ is the moisture activity at the first temperature T1 and $a_{wT2}$ is the moisture activity at the second temperature T2 and B is a constant for the type of oil used, and T is temperature of the oil in Kelvin.

14. The method of claim 10, further comprising the step of plotting the first and second moisture equilibrium curves, and graphically displaying the plots of the first and second moisture equilibrium curves.

15. The method of claim 1 further comprising the step of calculating an estimation of life lost of insulation over a period of time.

16. The method of claim 1 further comprising the step of calculating an estimation of total depolymerisation of insulation over a period of time.

17. A system adapted to determine polymerisation of transformer insulation, the system comprising:
   a transformer;
   at least one sensor adapted to measure moisture activity of oil and temperature of the transformer; and
   a processor configured to:
   receive a first moisture activity of oil in the transformer from the at least one sensor;
   receive a first temperature of the transformer from the at least one sensor;
   receive a second moisture activity of oil in the transformer from the at least one sensor;
   receive a second temperature of the transformer from the at least one sensor; and
   calculate a ratio of gradients of moisture equilibrium curves associated with the first moisture activity and the first temperature and the second moisture activity and the second temperature, wherein a moisture content of paper of the transformer is assumed to be substantially constant between the first temperature and the second temperature.

18. The system of claim 17, wherein the system comprises two sensors comprising:
   a capacitive oil sensor to measure the moisture activity of oil of the transformer; and
   a temperature sensor to measure the temperature of the transformer.

19. The system of claim 17, wherein the processor is further configured to:
   calculate a first water content of oil based on the first moisture activity and the first temperature; and
   calculate a second water content of oil based on the second moisture activity and the second temperature,
   wherein the step of calculating the ratio of gradients comprises using the first water content of oil associated with the first moisture activity and the first temperature and the second water content of oil associated with the second moisture activity and the second temperature.

20. A method for determining polymerisation of insulation of a transformer, the method comprising the steps of:
   measuring temperature data of a transformer at predefined intervals and simultaneously measuring moisture activity of oil data of the transformer;
   storing the moisture activity data and the temperature data in a database;
   accessing the moisture activity data and the temperature data from the database;
   calculating a difference between the temperature data at a first of the predefined intervals and the temperature data at a second of the predefined intervals;
   whereby:
   if the difference is not equal to 0,
   calculating a ratio of gradients of moisture equilibrium curves associated with the moisture activity data and the temperature data at the first of the predefined intervals and the moisture activity data and the temperature data at the second of the predefined intervals, wherein a moisture content of paper of the transformer is assumed to be substantially constant between the temperature data at a first of the predefined intervals and the temperature data at a second of the predefined intervals; and
   if the difference is equal to 0, calculating a difference between the temperature data at the first of the predefined intervals and the temperature data at a third of the predefined intervals.

\* \* \* \* \*